United States Patent [19]

Rasmussen et al.

[11] Patent Number: 4,844,870

[45] Date of Patent: Jul. 4, 1989

[54] LIQUID MONITORING

[75] Inventors: James Rasmussen, Plainville; Theodore S. Geiselman, Groveland, both of Mass.

[73] Assignee: Fisher Scientific Company, Pittsburgh, Pa.

[21] Appl. No.: 74,934

[22] Filed: Jul. 17, 1987

[51] Int. Cl.⁴ ............................................. G01N 21/01
[52] U.S. Cl. ..................................... 422/68; 222/185; 250/577; 356/246; 356/440; 422/63; 73/293
[58] Field of Search .................... 422/63–68, 422/81, 100; 73/293; 250/574, 576, 577; 356/440, 445, 246; 222/66, 185, 501

[56] References Cited

U.S. PATENT DOCUMENTS

| | | | |
|---|---|---|---|
| 3,808,887 | 5/1974 | Buttriss | 73/293 |
| 4,168,294 | 9/1979 | Calzi et al. | 422/68 |
| 4,219,530 | 8/1980 | Kopp et al. | 422/81 |
| 4,247,784 | 1/1981 | Henry | 250/577 |
| 4,304,257 | 12/1981 | Webster | 251/331 |
| 4,338,279 | 7/1982 | Orimo et al. | 422/64 |
| 4,440,022 | 4/1984 | Mason | 73/293 |
| 4,483,823 | 11/1984 | Umetsu et al. | 422/67 |
| 4,508,970 | 4/1985 | Ackerman | 250/577 |
| 4,534,651 | 8/1985 | Minikane | 422/64 |
| 4,601,881 | 7/1986 | Webster | 422/67 |
| 4,733,095 | 3/1988 | Kurahashi et al. | 73/293 |
| 4,745,929 | 5/1988 | Silver | 128/771 |
| 4,788,444 | 11/1988 | Williams | 250/577 |

Primary Examiner—Michael S. Marcus
Assistant Examiner—D. John Griffith, Jr.

[57] ABSTRACT

A liquid monitoring system includes chamber structure with a monitoring region in which the liquid to be monitored is disposed, the monitoring region having two spaced wall portions and a supplemental wall portion. The system further includes a radiation source mounted adjacent one of the spaced wall portions or directing a beam of radiation along a horizontal path, and a sensor mounted adjacent the opposed wall portion for receiving radiation in a beam path. The incident radiation beam as it passes through the wall into the monitoring region is refracted at the region surface as a function of gas or liquid within the region. At a first refracting angle, the refracted beam impinges on the supplemental wall and is internally reflected, the reflected radiation passing along a reflected beam path and sensed by the detector to provide an indication of the fluid in the chamber. At a second refracting angle, the refracted beam is not reflected in a direction such that radiation from the source is sensed.

7 Claims, 4 Drawing Sheets

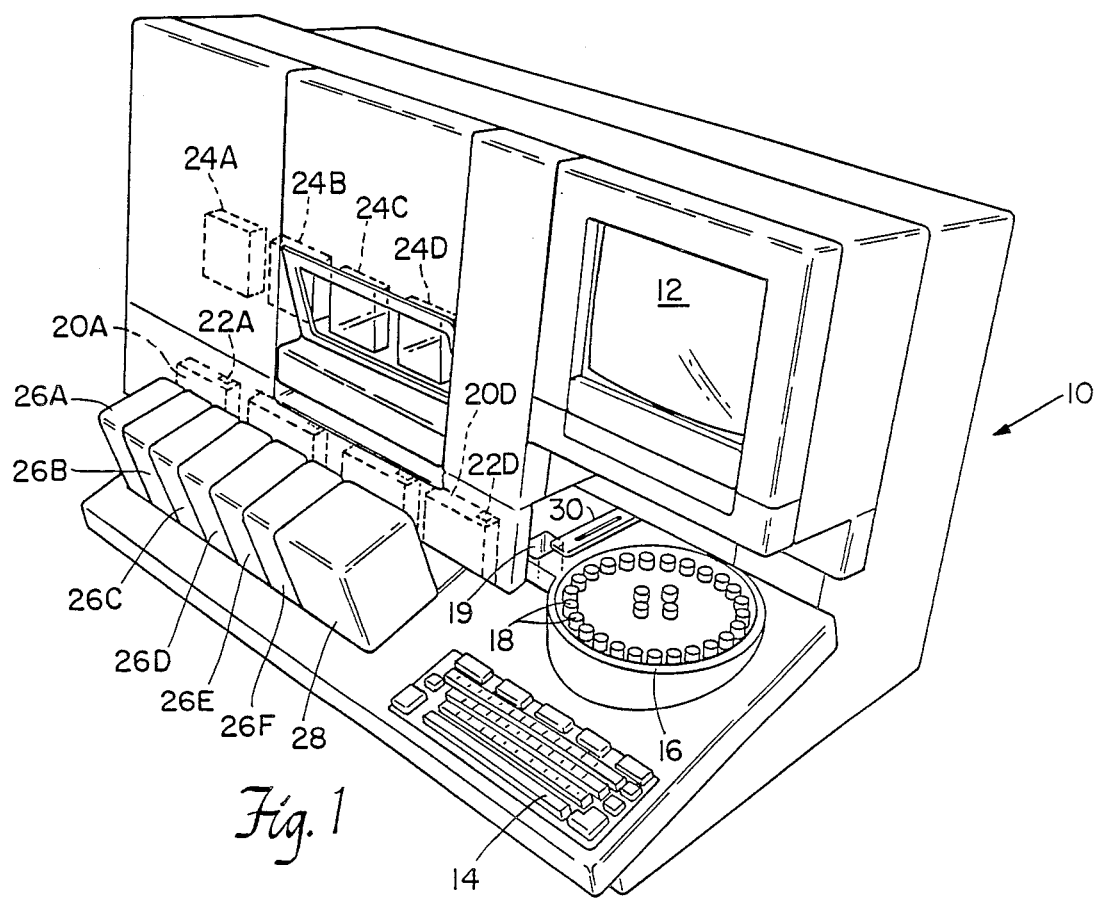
Fig. 1
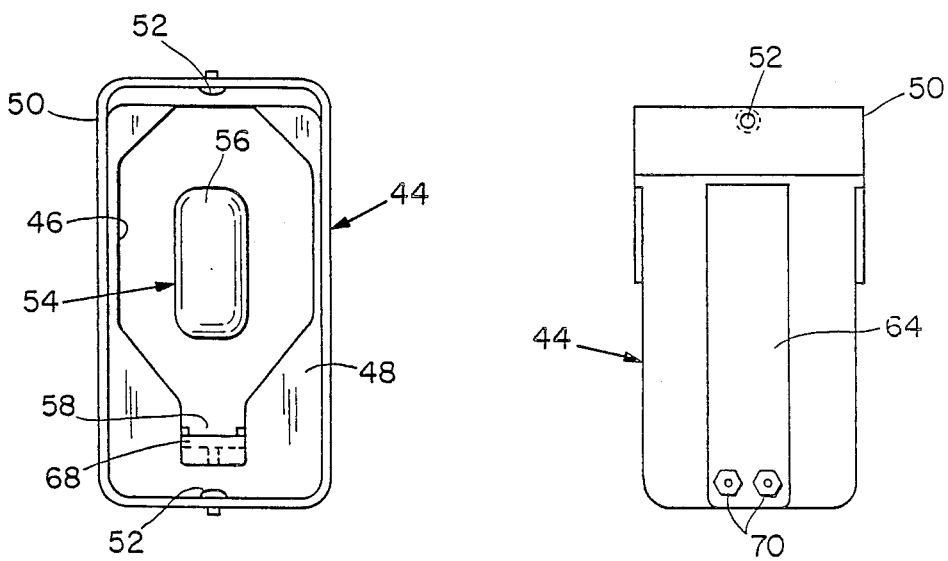
Fig. 3
Fig. 4

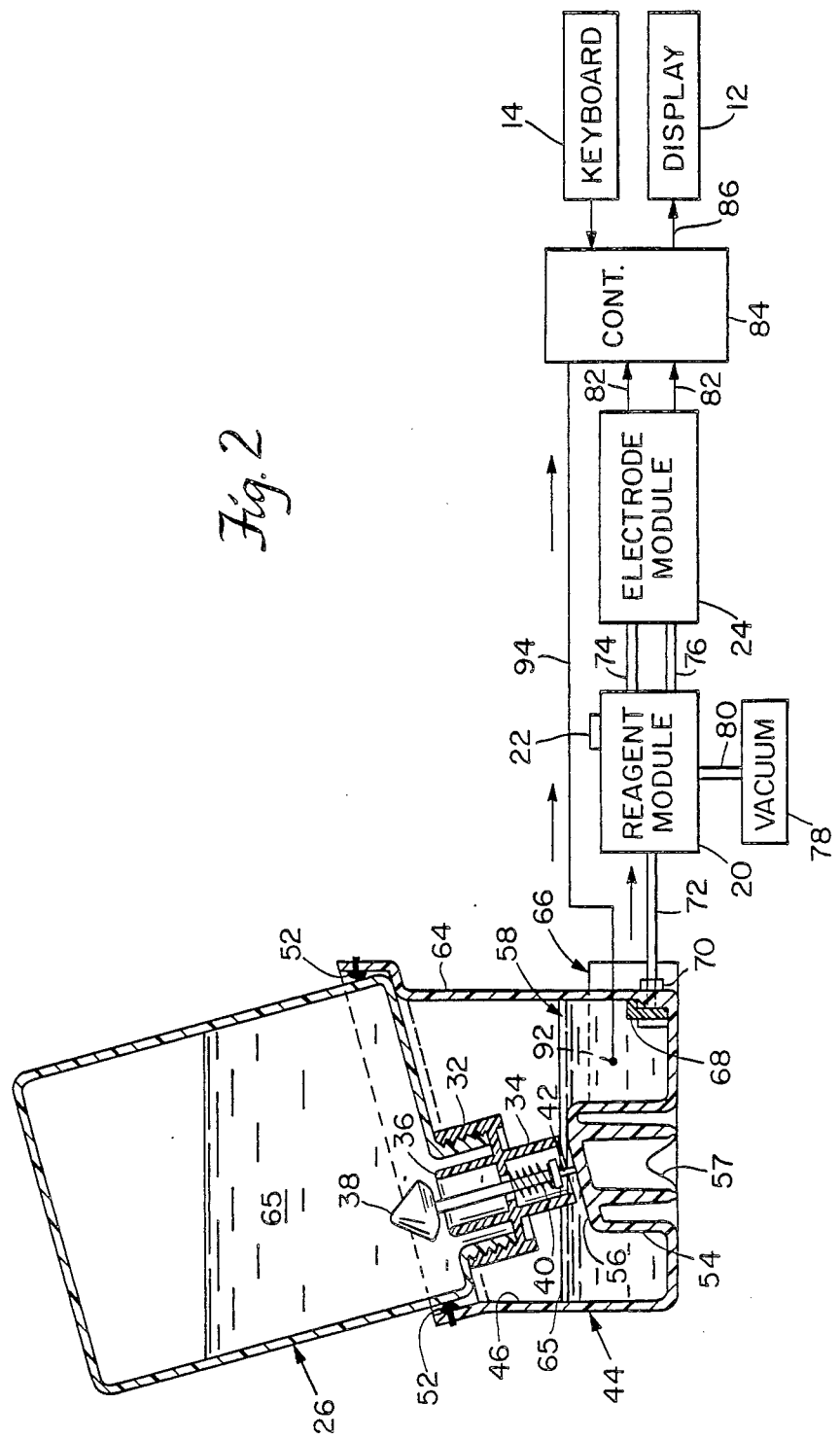

LIQUID MONITORING

This invention relates to liquid handling systems and has particular application to systems for handling reagents and the like in the analysis of biological fluids.

A variety of systems have been developed for the analysis of liquid samples. Frequently, in such systems, the sample to be analyzed is diluted or mixed with a reagent prior to analysis. The diluent or reagent to be mixed with the sample is drawn from storage, and it is desirable to monitor the quantity of diluent or reagent remaining in storage as should the diluent or reagent be depleted, the desired dilution ratio or reaction product will no be obtained and the resulting analytical values will be inaccurate or unreliable.

In accordance with one aspect of the invention, there is provided a liquid monitoring system that includes chamber structure with a monitoring region in which the liquid to be monitored is disposed, the monitoring region having two spaced wall portions and a supplemental wall portion. The system further includes a radiation source mounted adjacent one of the spaced wall portions for directing a beam of radiation along a horizontal path, and a sensor mounted adjacent the opposed wall portion for receiving radiation in a beam path. The incident radiation beam as it passes through the wall into the monitoring region is refracted at the region surface as a function of gas or liquid within the region. At a first refracting angle, the refracted beam impinges on the supplemental wall and is internally reflected, the reflected radiation passing along a reflected beam path and sensed by the detector to provide an indication of the fluid in the chamber. At a second refracting angle, the refracted beam is not reflected in a direction such that radiation is sensed.

In a particular embodiment, liquid monitoring apparatus in accordance with the invention is incorporated into a clinical analyzer system that employs a plurality of reagents and a plurality of sensor regions, each sensor region including one or more constituent sensors (for example, an ion selective electrode, a pH sensor or a photometric sensor). The system has a plurality of container structures that are positioned in inverted position in well type chamber structures and a source-sensor assembly is coupled to a monitoring region portion of each well-type chamber at a liquid level position at which a predetermined number of additional analyses using that liquid can be performed. The system controller includes an indicator which is tripped when the associated source-sensor assembly indicates that the liquid level is below the reference level and displays an indication to alert the operator to replace the container without interruption of analyzer operation. Should the analyzer controller count down to zero before a reagent container is replaced, system operation is halted to prevent loss of data or damage to the analysis system.

In a particular embodiment, the chamber structure includes a well of transparent polymeric material that has well portions of about two millimeters thickness and the monitoring region portion includes parallel opposed walls that are spaced about two centimeters apart and a bridging wall that is perpendicular to those walls. A unitary-sensor support assembly positions the radiation source and detector in angled relation to one another and bridges the monitoring portion of the chamber well with a radiation beam from the source being refracted at the fluid polymer interface of one wall. Flow of liquid from the container is controlled by the level of liquid in the chamber well relative to a container cap outlet port. On insertion of an inverted container into the chamber support structure, a container valve is opened as the container is initially engaged by frictional positioning abutment members and liquid is released from the container until the liquid level rises to the outlet port of the cap. When liquid in the well chamber is above the radiation beam path, the radiation beam impinges on the bridging wall for internal reflection to produce a reflected beam that is refracted at the opposed wall and sensed by the sensor. When the liquid level drops below that beam path, the polymer fluid interface refraction angle changes so that the incident beam is not internally reflected and the signal output of the detector drops.

The monitoring system thus provides an output signal indicative of the presence of the liquid being monitored, the absence of that signal providing an indication of the necessity to replace a reagent container. The system has fail safe characteristics as failure of the radiation source or obstruction of the radiation beam will cause a similar change in sensor output which provides an indication of the need to replace the indicated reagent container.

The invention provides convenient and reliable arrangements for monitoring liquid levels and is suitable for use in clinical analyzer systems. Other features and advantages of the invention will be seen as the following description of a particular embodiment progresses, in conjunction with the drawings, in which:

FIG. 1 is a perspective view of a clinical analyzer system in accordance with the invention;

FIG. 2 is a diagrammatic view of components of the liquid monitoring system employed in the system shown in FIG. 1;

FIG. 3 is a top plan view of well chamber structure of the liquid montoring system;

FIG. 4 is an end view of the well chamber structure shown in FIG. 3;

DESCRIPTION OF PARTICULAR EMBODIMENT

Figure 5:
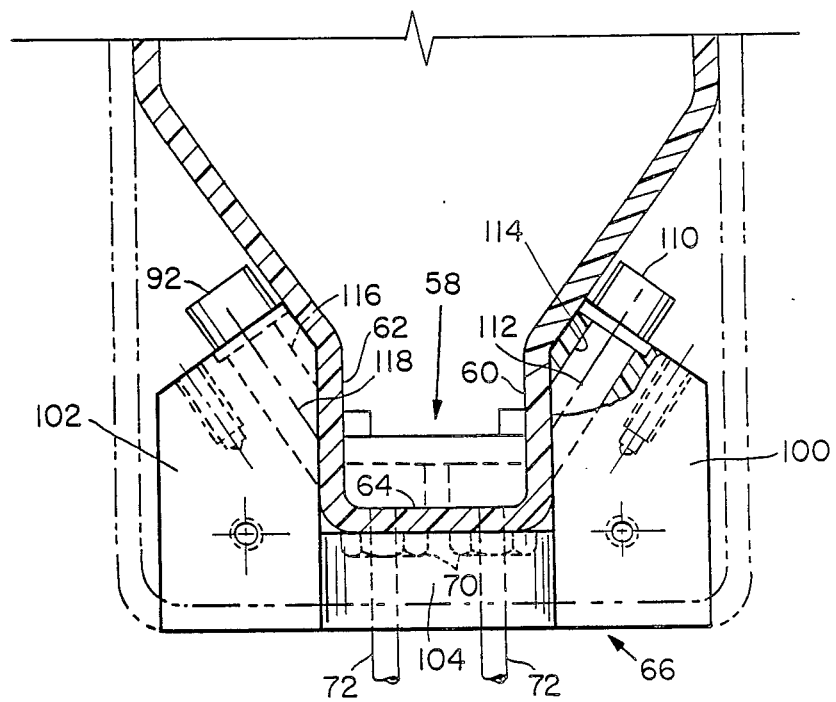
FIG. 5 is a sectional view taken along the line 5-5 of FIG. 6 showing aspects of the liquid monitoring system.

Shown in FIG. 1 is a perspective view of a bench top, chemistry/electrolyte analyzer 10 that is arranged for measuring calcium, carbon dioxide, chloride, creatinine, glucose, potassium, sodium and urea nitrogen constituents of samples of biological fluids such as serum, urine, and CFS. Analyzer 10 includes display 12, input keyboard 14, sample tray 16 that includes positions for forty sample cups 18 and four stat samples, wash station 19, four integrated fluidic modules 20A-20D, each with an inlet valve 22, four associated sensor modules 24, six associated reagent containers 26A-F, and rinse liquid container 28. Sample liquids to be analyzed are transported by probe assembly 30 from containers 18 to fluidic modules 20. Further details of that system may be had with reference to copending application Ser. No. 074,942, entitled Liquid Handling filed concurrently herewith, the disclosure of which is specifically incorporated herein by reference.

With reference to FIG. 2, each container 26, 28 includes a cap 32 with external tubular projection 34 that defines an outlet port and internal tubular projection 36 that defines a valve seat. Valve member 38 is biased to closed position on projection 36 by spring 40. Valve operating member 42 projects from sleeve 34 when valve 38 is closed.

With reference to FIGS. 2-6, well structure 44 is of molded acrylic resin and includes chamber structure 46 with container receiving surface 48 inclined at a 15° angle and rim structure 50 that carries friction member 52. Protrusion 54 is disposed in chamber 46 and has inclined valve actuator surface 56. A Tinnermann clip 57 in the base of protrusion 54 secures the well structure 44 in the analyzer. When reagent container 26 is inserted in inverted position in well 44, container 26 seats on container support surface 48 and friction members 52 engages the container body. Valve operator 42 engages protrusion 54 and is retracted and opens valve 38 such that liquid 65 flows into chamber 46. Monitoring region 58 has spaced parallel wall portions 60, 62 and bridging wall portion 64 that receives sensor assembly 66.

Filter 68 is at the base of chamber 46 and outlet fittings 70 are coupled by lines 72 to fluidic module 20. Outlet line 74 is connected to the corresponding sensor module 24 and line 76 returns to module 20. A source of reduced pressure 78 is connected to fluidic module 20 by line 80. Outputs from electrode module 24 are applied over lines 82 to controller 84 and controller 84 in turn provides outputs on lines 86 to display 12. Sensor assembly 66 includes sensor 92 that applies an output indicative of the presence or absence of liquid in well 46 over line 94 to controller 84.

Well structure 44 is formed of acrylic plastic and has a wall thickness of about two millimeters and chamber portion 46 is of generally octagonal configuration (as indicated in FIG. 3). Container receiving rim 50 is of rectangular configuration and defines an opening of about five centimeters width and about nine centimeters long and is adapted to receive a container 26 of about one half liter capacity. Valve actuator protrusion 54 extends about three centimeters above the base of chamber 46 and its upper surface 56 has rounded edges and is inclined at an angle of about 15° to the horizontal with a length of about three centimeters and a width of about 1½ centimeters.

Figure 6:
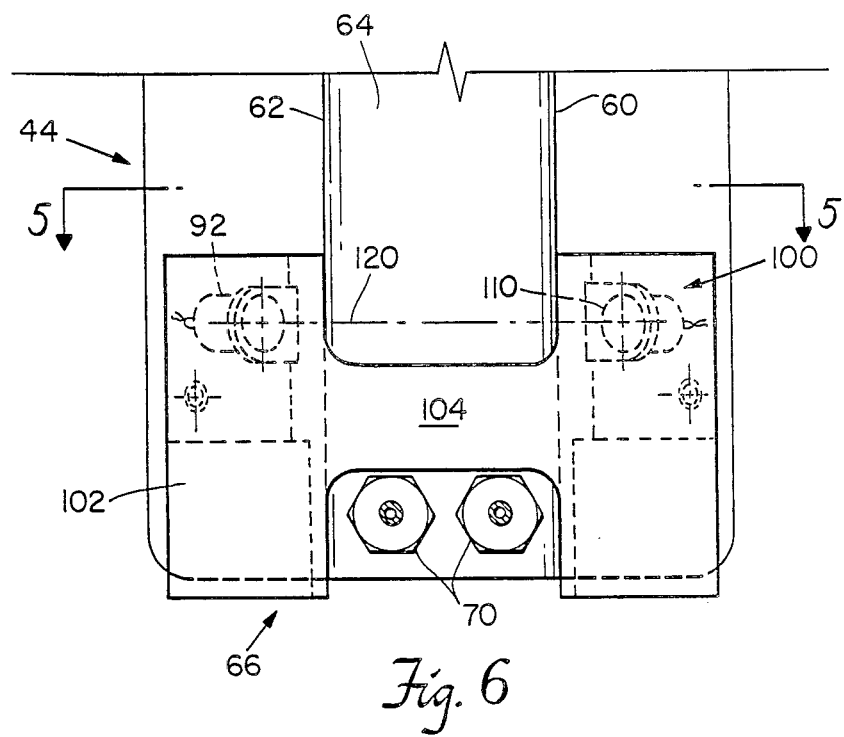
FIG. 6 is an end view of a portion of the well chamber and sensor assembly.

Formed at one end of chamber 46 is monitoring region 58 that has parallel walls 60, 62 and end wall 64. Sensor assembly 66, as shown in FIGS. 5 and 6, has plastic body with arm portions 100, 102 that have their inner surfaces spaced about two centimeters apart for receiving the projecting monitoring region portion 58 of well structure 44. Connecting web 104 is disposed above fittings 70. Carried in arm 100 is radiation source 110 that directs radiation along path 112 in passage 114. Radiation sensor 92 is similarly carried by arm 102 and receives radiation through passage 116 along beam path 118. The beam paths 112, 118 define a plane 120 (as indicated in FIG. 6) which is located about two centimeters above the base of well 44.

Figure 7:
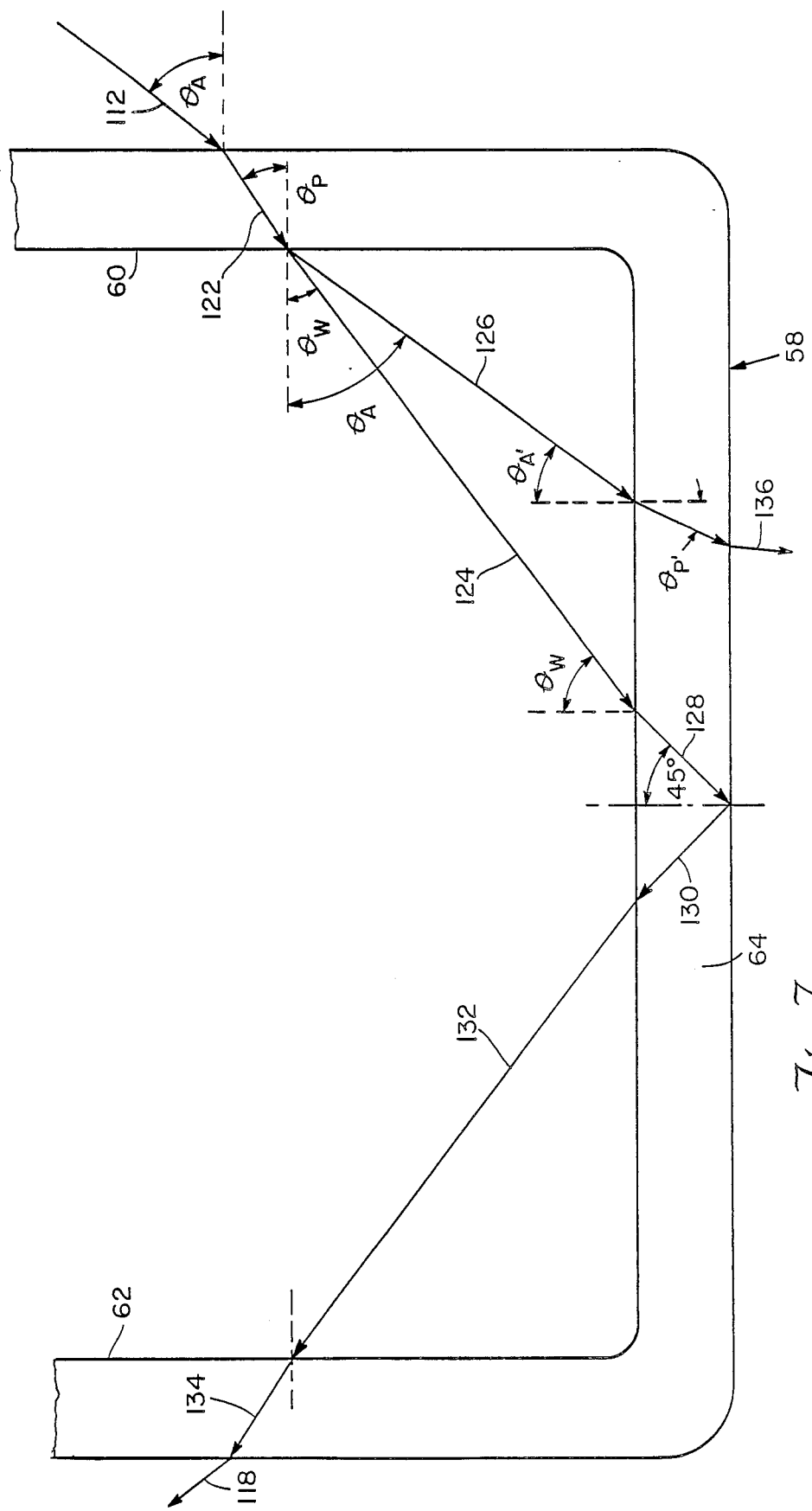
FIG. 7 is a diagrammatic view showing radiation beam paths in the liquid monitoring system shown in FIG. 2.

A diagram of the radiation beam path through monitoring chamber region 58 is shown in FIG. 7. That chamber region has spaced parallel walls 60, 62 that are connected by end wall 64. The incident beam of radiation along beam path 112 impinges on the outer surface of wall 60 at the angle $\theta_A$ (about 54°) and is refracted along path 122 in the acrylic wall 60 at an angle $\theta_P$ (about 33°). At the inner surface of wall 60, the beam is again refracted at an angle $\theta_W$ (about 38°) along path 124 if that interface is an acrylic-liquid interface and at an angle $\theta_A$ (about 54°) along path 126 if that interface is an acrylic-air interface.

In the case of beam 124 (an acrylic-liquid interface), the beam impinging on end wall 64 is refracted along path 128 and impinges on the outer surface of wall 64 at an angle of about 45° where the beam is totally internally reflected along path 130 and similarly refracted at the wall-liquid interface along path 132; refracted at the second liquid-acrylic interface along path 134 and again refracted at the air acrylic interface along path 118 for sensing by sensor 92 which produces an output signal on line 94 to the controller 84 providing an indication that the beam is passing through liquid in the monitoring portion of the chamber. Should the beam not be refracted along path 124 but along path 126, it impinges on the wall 64 and is refracted at an angle of $\theta_P{}'$ (an angle of about 23°) and is further refracted along path 136 rather than being reflected so that the radiation beam does not reach sensor 92.

Thus, when liquid of refractive index corresponding approximate to that of water is in the sensor well at a level of the sensing plane 120, sensor 92 responds from radiation from source 110 and produces an output on line 94 which signals controller 84 that there is liquid for at least ten more test cycles is in the well 46. When the liquid level falls below sensor plane 120, the output of sensor 92 changes and controller 84 produces a low level indication at display 12. In the analyzer shown in FIG. 1, similar sensor systems are provided for monitoring each of the reagent containers 26 and rinse liquid container 28. The level of the output signal from the respective sensor changes from 4.9 volts in the presence of the rinse liquid (distilled water) to 0.16 volts in its absence; from 4.6 volts when it passes through an ion selective electrode reference solution to 0.16 volts in the absence of that liquid; and from 4.9 volts when it passes through a creatinine reagent to 0.16 volts when the reagent level falls below the reference plane.

While a particular embodiment of the invention has been shown and described, various modifications thereof will be apparent to those skilled in the art, and therefore, it is not intended that the invention be limited to the disclosed embodiment or to details thereof, and departures may be made therefrom within the spirit and scope of the invention.

What is claimed is:

1. A liquid monitoring system comprising
   chamber structure in which the liquid to be monitored is adapted to be disposed, said chamber structure including a monitoring region that has two spaced wall portions and a supplemental wall portion therebetween,
   radiation source means mounted adjacent one of the spaced wall portions for directing an incident beam of radiation along a horizontal path in a direction oblique to said one wall portion through said one wall portion for refraction by the fluid in said monitoring region and impingement on said supplemental wall portion, said incident radiation beam as it passes through said one wall portion into the monitoring region being refracted at the region surface at a refraction angle as a function of gas or liquid within the region, and
   radiation sensor means mounted adjacent the other spaced wall portion for receiving radiation in said incident radiation beam that is reflected by said supplemental wall portion.

2. The system of claim 1 wherein said chamber structure includes a well of transparent polymeric material an said monitoring region portion includes opposed walls that are spaced apart and define said two spaced wall portions, and a bridging wall that defines said supplemental wall portion and interconnects said opposed walls, and further including unitary source-sensor support structure for positioning said radiation source and sensor means in angled relation to one another.

3. The system of claim 2 wherein said opposed walls are parallel to one another and said bridging wall is perpendicular to said opposed walls.

4. A clinical analyzer system comprising a plurality of sensor region, each sensor region including at least one constituent sensor,
 a plurality of fluidic modules, each said fluidic module being coupled to a corresponding one of said sensor regions and including a sample input and an auxiliary liquid input,
 a plurality of well-type chamber structures, each said well-type chamber structure having a monitoring region portion, and a source-sensor assembly coupled to each said monitoring region portion of each said well-type chamber at a reference liquid level position at which a predetermined number of additional analyses can be performed,
 said monitoring region portion having two spaced wall portions and a supplemental wall portion,
 said source-sensor assembly including radiation source means mounted adjacent one of said spaced wall portions for directing an incident beam of radiation along a horizontal path in a direction oblique to said one wall portion for refraction by the fluid in said monitoring region portion and impingement on said supplemental wall portion, and radiation sensor means mounted adjacent the other spaced wall portion for receiving radiation reflected by said supplemental wall portion, said incident radiation beam as it passes through the wall into the monitoring region being refracted at the region surface at a refraction angle as a function of the fluid within the region,
 each said well-type chamber structure being adapted to receive container structure, each said container structure including an outlet for flowing liquid from said container structure into said well-type chamber, each said well-type chamber structure being coupled to a corresponding fluidic module for flowing an auxiliary liquid to said fluidic module,
 controller means including an indicator which is tripped when an associated source-sensor assembly indicator that the liquid level is below said reference level, and
 output means responsive to said controller means for providing an indication to alert the operator to replace a container without interruption of analyzer operation.

5. The system of claim 4 wherein said chamber structure includes a well of transparent polymeric material and said monitoring region portion includes opposed walls that are spaced apart and define said two spaced wall portions, and a bridging wall that defines said supplemental wall portion and interconnects said opposed walls, and said source-sensor assembly includes unitary source-sensor support structure for positioning said radiation source and sensor means in angled relation to one another.

6. The system of claim 4 and further including container structure that has a valved outlet and that is adapted to be inserted into a corresponding well-type chamber structure in inverted relation, said valved outlet being opened as the container is initially inserted and liquid being released from the container until the liquid level in said well-type chamber structure rises above the outlet of said container.

7. A method of monitoring liquid level comprising the steps of
 providing a well-type chamber structure, said well-type chamber structure having a monitoring region portion and said monitoring region portion having two spaced wall portions and a supplemental wall portion therebetween,
 directing an incident beam of radiation along a horizontal path in a direction oblique to one of said wall portions through said one wall portion for refraction by the fluid in said monitoring region portion and impingement on said supplemental wall portion, and
 receiving radiation in said incident radiation beam that is reflected by said supplemental wall portion, said incident radiation beam as it passes through the wall into the monitoring region being refracted at the region surface at a refraction angle as a function of the fluid within the region.

* * * * *